(12) United States Patent
Müller (10) Patent No.: US 10,588,643 B2
(45) Date of Patent: Mar. 17, 2020

(54) SURGICAL TRABECULAR TOOL AND METHOD FOR MANUFACTURING

(71) Applicant: Erich Johann Müller, Kleinwallstadt (DE)

(72) Inventor: Erich Johann Müller, Kleinwallstadt (DE)

(*) Notice: Subject to any disclaimer, the term of this patent is extended or adjusted under 35 U.S.C. 154(b) by 140 days.

(21) Appl. No.: 15/370,273

(22) Filed: Dec. 6, 2016

(65) Prior Publication Data

US 2018/0132866 A1    May 17, 2018

(30) Foreign Application Priority Data

Nov. 14, 2016    (EP) ..................................... 16198683

(51) Int. Cl.
| | |
|---|---|
| *A61B 17/16* | (2006.01) |
| *B33Y 10/00* | (2015.01) |
| *B33Y 50/02* | (2015.01) |
| *B33Y 80/00* | (2015.01) |
| *A61B 17/00* | (2006.01) |

(52) U.S. Cl.
CPC ...... *A61B 17/1635* (2013.01); *A61B 17/1615* (2013.01); *A61B 17/1659* (2013.01); *A61B 17/1666* (2013.01); *B33Y 10/00* (2014.12); *B33Y 50/02* (2014.12); *B33Y 80/00* (2014.12); *A61B 17/1617* (2013.01); *A61B 2017/00526* (2013.01)

(58) Field of Classification Search
CPC . A61B 17/16; A61B 17/1615; A61B 17/1635; A61B 17/1659
See application file for complete search history.

(56) References Cited

U.S. PATENT DOCUMENTS

| | | | |
|---|---|---|---|
| 6,120,508 A | 9/2000 | Gruenig et al. | |
| 2011/0202060 A1 | 8/2011 | White et al. | |
| 2016/0332236 A1* | 11/2016 | Stoyanov | ................ B23B 27/14 |
| 2017/0000502 A1* | 1/2017 | Mroczkowski | .... A61B 17/1666 |

* cited by examiner

*Primary Examiner* — Christopher J Beccia
(74) *Attorney, Agent, or Firm* — Whiteford, Taylor & Preston, LLP; Barry E. Bretschneider (57) ABSTRACT

A surgical trabecular tool for manipulating or removing bone tissue includes a tool body and at least one cutting element provided on the tool body. The cutting element includes a number of cutting edges arranged thereon, and the tool body is formed at least in part by a trabecular internal structure including a plurality of material struts forming a regular or irregular lattice structure which supports and connects the cutting elements.

11 Claims, 8 Drawing Sheets

SURGICAL TRABECULAR TOOL AND METHOD FOR MANUFACTURING

REFERENCE TO RELATED APPLICATIONS

This application claims the priority of European Application No. 16 198 683.1, filed Nov. 14, 2016, the entire contents of which are incorporated herein by reference.

FIELD OF THE INVENTION

The present invention relates to surgical instruments for bone machining, i.e. for example for drilling, rasping, removing or otherwise mechanically manipulating bone tissue. In particular, the invention relates to an adaptive disposable bone machining instrument and a method for manufacturing such an instrument.

BACKGROUND OF THE INVENTION

In orthopedic surgery and in particular implant surgery, various instruments for removing or machining bone tissue are well known, such as milling tools, surgical fraises, reamers, drills, rasps, and others. Such instruments may present in various different forms, each adapted to the specific cavity required within the bone tissue. For example, instruments may be generally spherical or hemispherical, cylindrical, tapered, or more complicated combinations of shapes.

Any of those tools may be designed for use as a hand tool or a machine tool, and may thus also be provided with adaptors or connection elements for grips, driving elements or further options.

In order to minimize any risk of infection during surgery, instruments and tools are increasingly provided as disposable tools for single use. Such instruments need to fulfil certain characteristics:

- providing optimal precision in order to provide a stable bone cavity for primary stability of an implant, and to obtain required surface quality;
- obtaining a bone cavity essentially free of bone and cartilage chippings and cuttings, so that any need for rinsing and suctioning of the cavity during surgery is minimized;
- reduced cutting resistance for reamers and fraises, and reduced intramedullary pressure;
- reducing manufacturing costs;
- easy collection of bone material, e.g. for grafting;
- simple and secure disposal of single-use instruments.

An example of a disposable surgical reamer is given by US patent application No. 2011/0202060A1, where the reamer is assembled from multiple parts. A hemispherical surface with cutting elements is combined with a base element and internal structural supports. Further examples are given in U.S. Pat. No. 6,120,508, disclosing a disposable bone rasp.

While there are surgical instruments which fulfil some of these criteria, there is a need for an improved tool and manufacturing method which optimizes all required features.

SUMMARY OF THE INVENTION

The present invention discloses a disposable surgical instrument and a method for producing said disposable surgical instrument in accordance with the appended independent claims. The dependent claims describe preferred embodiments.

Generally, material requirements are reduced considerably by providing a surgical tool with an internal lattice structure which is at least partially formed by a lattice of material bars or struts, such as a honeycomb structure, while maintaining structural stability and cutting forces of the tool. The structure may be similar to a trabecular structure known from bone tissue and may therefore also be termed "trabecular structure" for purposes of this invention. Tools with such trabecular internal structures may be manufactured using three-dimensional additive manufacturing methods. Required strut thicknesses, lattice dimensions and further structural features for the manufacturing process may be obtained from numerical modelling for each application.

In this way, custom-made surgical tools with considerably reduced manufacturing costs and optimal characteristics are provided.

According to the invention a surgical tool for manipulating or removing bone tissue is provided comprising a tool body; at least one cutting element provided on said tool body, said cutting element comprising a number of cutting edges arranged on said cutting element; wherein said tool body is formed at least in part by an internal trabecular structure including a plurality of material struts forming a regular or irregular lattice structure which supports and connects the cutting elements and surrounding inside empty recesses, starting with the inlets from the cutting edges. The cutting edges are preferably solid.

According to another aspect of the invention a surgical tool is provided, wherein said lattice structure is based on a circular, rectangular, triangular, hexagonal, or quadrangular base shape.

According to another aspect of the invention a surgical tool is provided wherein said trabecular lattice structure is an irregular structure, or wherein the lattice structure is one of a honeycomb, cubical, or pyramidal structure.

According to another aspect of the invention a surgical tool is provided, wherein said trabecular tool body structure is provided sustaining and connecting cutting elements along an inner cutting surface reverse dome structure.

According to another aspect of the invention a surgical tool is provided, wherein said trabecular internal structure includes multiple empty columns or recesses and with increasing volume extending from the inlets at an inner face of said cutting edges spirally towards the center and bottom of said tool body and ending in a central common cavity.

According to another aspect of the invention a surgical tool is provided, wherein said cutting elements including a plurality of cutting edges are arranged radially across the said cutting surface.

According to another aspect of the invention a surgical tool is provided, wherein said surgical tool is a bone reamer, rasp, fraise, or drill.

According to another aspect of the invention a surgical tool is provided, wherein said tool body is shaped hemispherically, spherically, tapered, or cylindrically.

According to another aspect of the invention a surgical tool is provided, wherein said cutting surface includes inlets for diverting bone and cartilage chippings away from said surface towards an inside of said tool body.

According to another aspect of the invention a surgical tool for manipulating or removing bone tissue is provided, comprising a tool body core, including multiple core rings fixedly attached to a lateral surface of said tool body core; at least one cutting element comprising multiple cutting edges on one side, and further comprising multiple guiding rings fixedly attached to a second side; wherein the top end of said cutting element is pivotably attached to a top end of said tool body core, and said core rings and said guiding rings are interlocked such that said cutting element is movably but limitedly connected to said tool body core.

According to another aspect of the invention a surgical tool is provided, wherein said tool body core is at least in part formed by a trabecular internal structure including a plurality of material struts forming a regular or irregular lattice structure.

According to another aspect of the invention a surgical tool is provided, wherein chain elements comprising multiple interlocked chain links are connected between said body core and said at least one cutting element, and/or between first and second cutting elements, preferably adjacent cutting elements.

According to another aspect of the invention a surgical tool is provided, wherein said core rings and said guiding rings are arranged such that said tool is capable of assuming an open stable position with maximum tool diameter and a closed position with reduced tool diameter.

According to another aspect of the invention a method for manufacturing a surgical tool is provided comprising forming at least a portion of said tool by a three-dimensional additive manufacturing process.

According to another aspect of the invention a method is provided, wherein said surgical tool is completely formed by said three-dimensional additive manufacturing process.

According to another aspect of the invention a method is provided, wherein said manufacturing process is one of laser sintering, laser melting, electron beam melting, lamination, 3d printing, extrusion deposition.

According to another aspect of the invention a method is provided, further comprising obtaining input variables for said surgical tool, said input variables including at least one of size, tool body, cutting elements and edges design, required cutting force, and material; numerically simulating an optimal internal structure based on a trabecular structure for said surgical tool using said input variables; and providing a result of said numerical simulation for use in said three-dimensional additive manufacturing process.

According to another aspect of the invention a method is provided, wherein said numerical simulating comprises a finite element method.

BRIEF DESCRIPTION OF THE DRAWINGS

Embodiments of the invention will further be described in more detail with reference to exemplary figures, wherein

FIG. 2.1 shows a vertical cross section of the reamer of FIG. 1,

FIG. 2.2 shows exemplary variants for the shape of the cutting elements along the reamer surface of FIG. 1;

FIG. 4.2 shows variants for the cutting edges of FIG. 1;

FIG. 5.1 is a partial vertical cross section of a reamer in the area of a cutting element with the supporting trabecular inner structure and the empty recesses starting from the cutting edges increasing to the axis;

FIG. 5.2 is a horizontal cross section of a reamer showing the cutting edges with the trabecular body structure forming also the outer coat and forming inside empty recesses;

FIG. 6.1 exemplifies various lattice structures for the internal structure of a surgical instrument;

FIG. 6.2 exemplifies a cross section on the external surface first parallel and second perpendicular on the cutting edges showing guiding protrusions on the external struts directed on the movement direction;

FIG. 6.3 shows cross sections of different struts section designs;

FIG. 17.1 is a bottom view of an expandable reamer for minimal invasive surgeries according to an embodiment of the invention in closed position;

FIG. 17.2 is a view of the reamer of FIG. 17.1 in expanded cutting position;

FIG. 21 depicts various elements suited for attachment to and handling of surgical tools according to the invention; and FIG. 22 shows an exemplary press device for disposing surgical tools and collecting grafting bone material according to the invention.

DETAILED DESCRIPTION OF EXEMPLARY EMBODIMENTS

Figure 1:
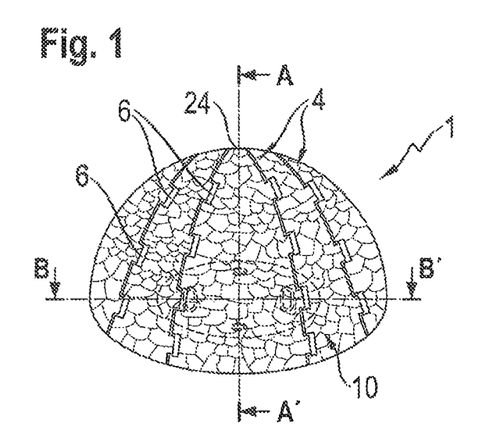
FIG. 1 shows an exemplary acetabular reamer with cutting elements and an inner structure.

FIG. 1 shows an acetabular reamer 1 according to a first embodiment of the invention. The invention is not limited to reamers or any particular kind of surgical instrument, although this reamer will be described in detail for understanding general ideas of the invention.

Acetabular reamers usually comprise a hemispherical surface 2 provided with cutting or rasping elements 4 such as a plurality of cutting edges 6 or teeth. These cutting edges 6 are disposed across the hemispherical surface 2 such that bone tissue can be removed by applying adequate pressure towards the bone and rotating the reamer 1 in a predefined direction.

According to the described example, cutting elements 4 are arranged in the form of multiple cutting edges 6 along lines which extend from the apex 24 of the hemispherical cutting surface 2 towards the bottom 26 of the hemisphere. Alternatively, a cutting element 4 can be formed as a single continuous cutting edge 6, or as a different geometrical arrangement of several cutting edges 6. Structural details of the cutting elements 4 will be described more thoroughly below. In general, the elements 4 may be formed by providing sharp cutting edges which protrude from the surface in relation to portions between the cutting edges. Orientation of the cutting edges may e.g. be parallel along the line arrangement of a cutting element, or edges may be oriented otherwise.

Figure 21:
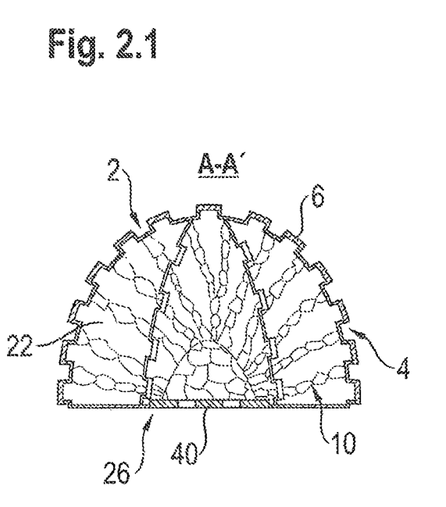

FIG. 1 and in particular the cross section depicted in FIG. 2 also show the inner structure of a surgical tool according to embodiments of the invention. The tool body 1 is, in part or completely, built as a trabecular inner structure 10 with lattice elements of various sizes and shapes, formed by material struts 12, rods or bars. Such structures are known from bone tissue as trabeculae, and the proposed structure is therefore referred to as a trabecular structure 10 in this description. Such a structure 10 may be a classic honeycomb structure, but may also include other lattice types such as cubical and pyramidal and irregular lattices, such as porous or foam-like structures or a mix of these structures. Also, the trabecular structures 10 may be present in certain portions of the tool body 1, while others are constructed in solid fashion, such as the cutting elements or link parts to the adaptors. Using trabecular structures within the tool body allows for reducing wall thickness and material consumption in general, due to the improved stability provided by the lattice, while at the same time maintaining required cutting forces and tool strength. Each lattice element is defined by the struts 12 forming the lattice. Such structures may also include open-cell foams, also referred to as reticulated foams. Basically, this describes a cell structure where only the edges remain, with the faces or walls missing. The lattice structure may be a regular lattice or an irregular structure.

However, the invention may also include lattice structures with closed or partially closed faces/walls, i.e. closed-cell foams or lattices. In all embodiments, the open lattice structures 10 according to the invention may be replaced by or combined with such (partially) closed-cell structures, and the term "trabecular" is intended to include both options for purposes of this invention. For purposes of this description, it should further be noted that the term "cutting surface" 2 is used in a geometrical sense for describing at least one outer face of the tool body carrying cutting elements/edges, and does not necessarily describe a continuous or closed surface; rather, the cutting edges 6 may preferably be supported directly by struts 12 of an open trabecular structure 10, as will be described below in more detail. Yet, a continuous surface or essentially continuous surface with cutting edges and corresponding inlets is also within the scope of this invention.

The struts or rods 12 forming the trabecular structure 10 may have different dimensions and geometries even within one structure, and in case of partially closed-cell lattice structures, the wall thickness and also of the surface of the tool may be constant or varying across the tool. All these characteristics are dependent on intended usage of the tool, structural features, forces and other variables. Material requirements may in this way be reduced down to 2-3% of total body volume, which lowers manufacturing cost considerably, especially n disposable tools. In other setups with more solid portions, more than 2-3 vol. % in material may be used for the tool body.

Figure 51:
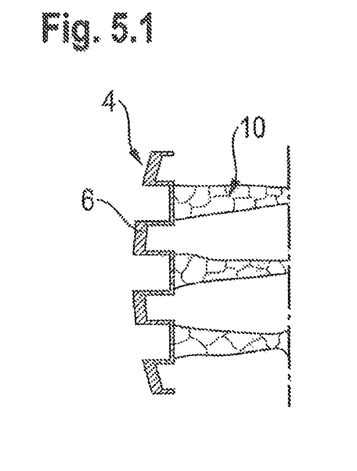
Figure 52:
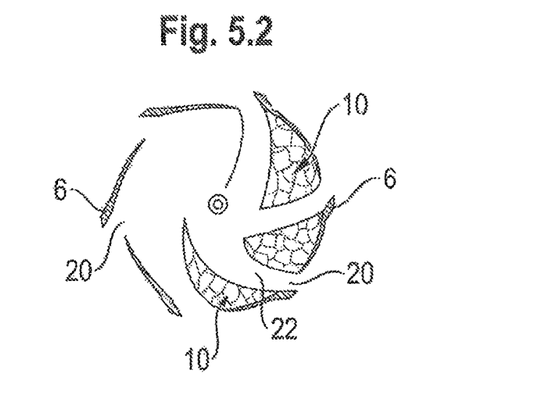

In FIG. 2, as an exemplary embodiment it is shown that trabecular structures 10 extend from the surface areas towards the center of the tool body, providing structural support for the hemispherical surface 2, while between those structures there are voids or cavities 22 forming channel structures. These channels 22 allow for diverting and containing bone and cartilage chippings, which therefore facilitates or obviates the need for cleaning of the bone cavity during surgery. The alternating trabecular 10 and void 22 structures are shown in more detail in the example of FIG. 5. As shown here, the column-like trabecular structures may decrease in width towards the center of the tool body 1 and may encapsulate increasing empty recesses, but may also have constant width or more complicated designs.

Apart from the structure shown in FIG. 2, almost any other combination of trabecular structures 10, voids 22, and solid structures is conceivable. For example, internal cross-sections of a tool may be star-shaped, or spiraling as in FIG. 5 or christmas-tree like for the rasp, but may also be shaped circular or rectangular.

Figure 22:
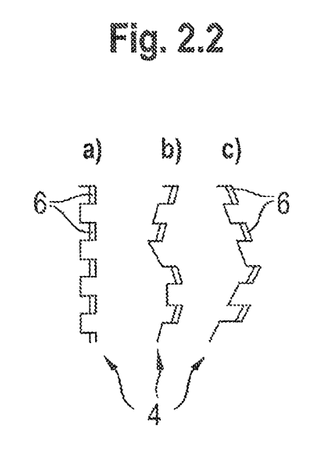

FIG. 2.2 shows variations of the cutting element arrangement, with each cutting element 4 being formed by an arrangement of one or more cutting edges 6. Lines of cutting elements across the tool surface 2 may be straight lines, i.e. straight lines projected on the surface, as in example a); also, cutting edges 6 may be arranged along undulating (b), inclined, or zig-zag (c) lines across the surface. Also, length of each cutting edge 6 and number of cutting edges 6 may vary along those lines; preferably, cutting edges near the apex 24 are longest and then lengths of the cutting edges are reduced towards the bottom 26 of a hemisphere.

This leads to improved centering of the reamer 1 and a more precise bone cavity. However, it is also possible to provide cutting edges of equal length, or to adapt location and edge length based on the force required at that specific location.

Figure 3:
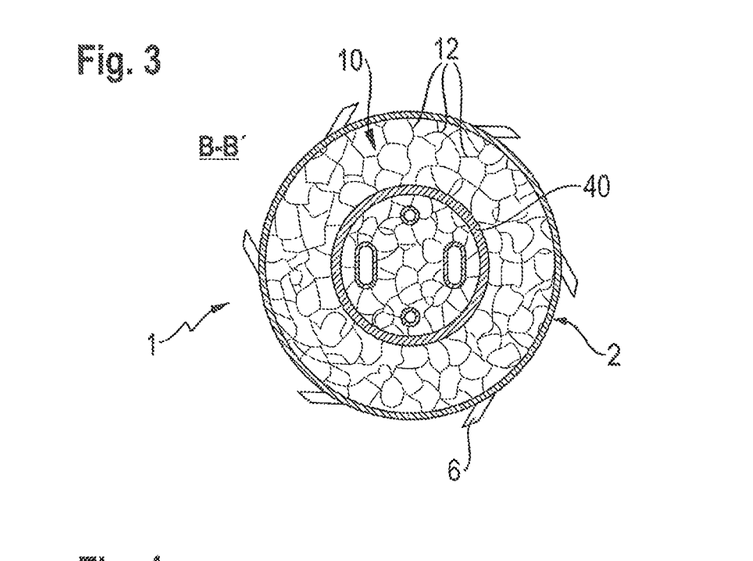
FIG. 3 is a bottom view of the reamer of FIG. 1.

FIG. 3 is a bottom view of an exemplary hemispherical reamer 1 across plane B-B as indicated in FIG. 1. Again, the trabecular structure 10 can be seen within the tool body. In addition, the tool bottom 26 comprises a connecting portion 40 such as an adapting or link plate and holes for fastening means that may be constructed in solid fashion. This connecting portion 40 may be used for connecting the surgical tool to handles, drive elements, rods, or other elements used for handling, moving, and driving the tool. Any common connecting system may be used, such as screws, snap-in elements, mounting threads, and others.

Figure 4:
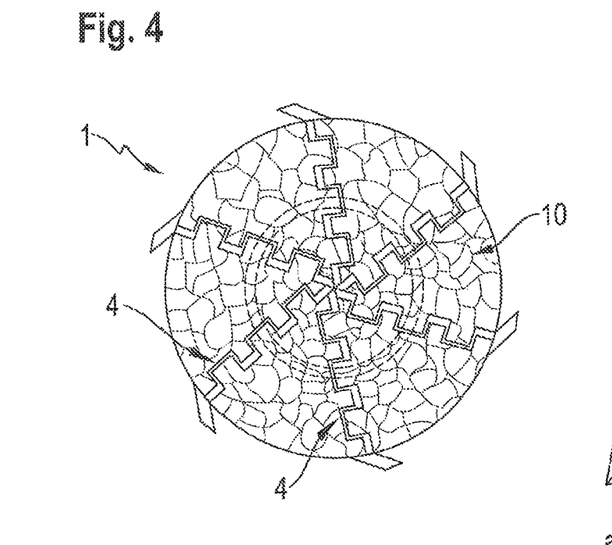
FIG. 4 is a top view of the reamer of FIG. 1.

FIG. 4 is a top view of an exemplary reamer 1. It can be seen that the cutting edges 6 are arranged along lines which extend radially across the hemispherical surface 2. As already mentioned, this is only one exemplary option for arranging cutting elements 4 on surgical tools according to the invention.

Figure 42:
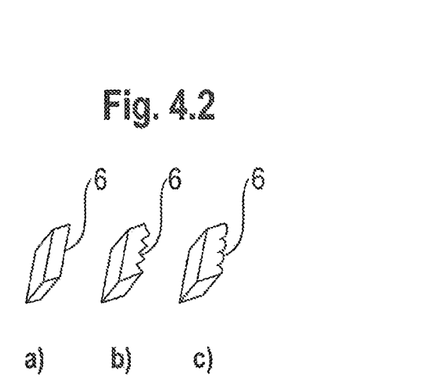

As can be seen in FIG. 4.2, the cutting elements 4 can further be varied by changing the edge structure of cutting edges 6. For example, cutting edges 6 may be smooth as in variant a), but might also comprise a toothed edge as in b) and/or edges with incisions along the blade as in c). Cutting edges 6 may be formed as "claws" with a number of half circled edges. In addition or alternatively, cutting edge geometry in cross section may be beveled edge, V-shaped, chisel edge, convex edge, or others. Different blade variants and/or edge geometries may also be combined across the tool surface.

Figures 61, 62, 63:
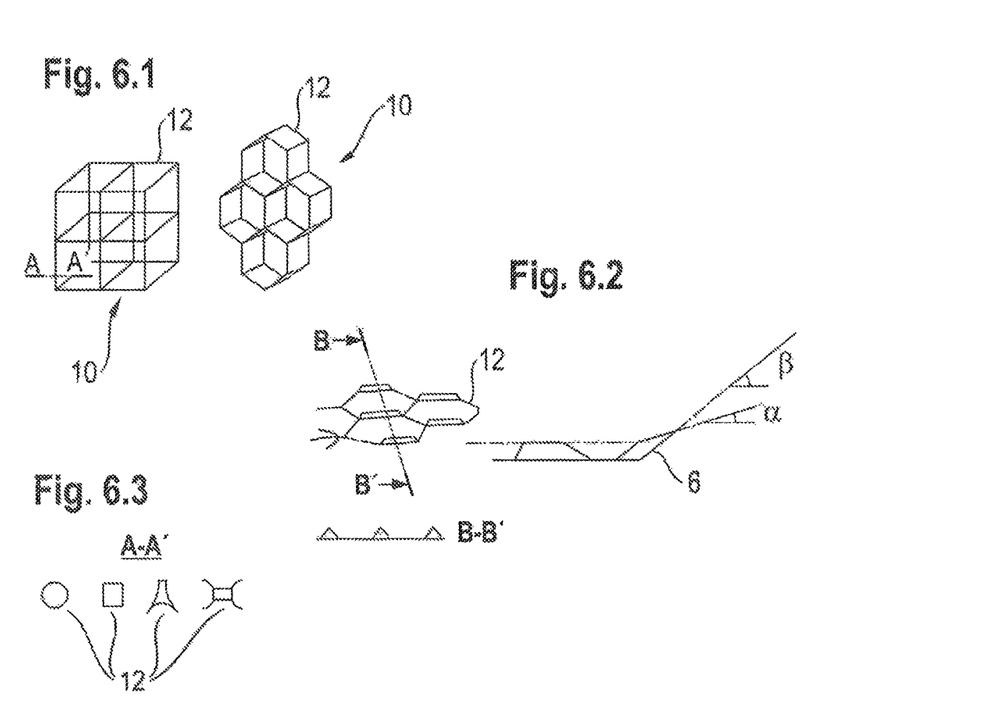

FIG. 6.1 shows some options for lattices of the trabecular structure 10 of the tool body 1 or portions of the tool body. Example 1 is a cubical lattice structure while example 2 is a hexagonal basic structure with rectangular side elements. As mentioned before, each of these structures 10 may preferably be formed by struts or bars 12 of predefined size, forming an open lattice, but might also comprise partially closed cell walls in some embodiments. Also, the trabecular structures 10 may be formed in a regular manner as shown in these figures, or may also be formed essentially irregular through to a foam-like or sponged material structure. Another option is a corrugated core structure, where two essentially flat layers are disposed on both sides of a corrugated stabilizing structure, forming a sandwiched layer. Exemplary regular lattice structures 10 are honeycomb, pyramidal or cubical structure.

FIG. 6.2 depicts a cross section of exemplary cutting edge 6 structures, with cutting angle α and clearance angle β indicated in the figure. Both angles α and β are designed as decreasing towards the bottom or equator of the tool in order to achieve self-centering during use. In case of a rasp, both cutting angles and clearing angles of the cutting edges 6 are similarly decreased, starting from the wedge axis (see FIG. 7 and description below) and decreasing towards peripheral regions of the rasp.

The trabecular struts may be based on any cross-section geometry, as shown in FIG. 6.3, such as a circular (1), rectangular (2), concave triangular (3), concave quadrangular (4), or any other cross-section.

As seen in FIG. 6.2, the peripheral trabecular structures 10 may be provided at different depth related to the tool surfaces. Those elements which are directed in rotational/moving direction of the tool are reinforced by the external tool surface and are partially elevated (see cross-section B-B' in FIG. 6.2), such that the elevated elements may act as additional guidance for maintaining cutting direction of the tool. The elements are elevated at most up to the level of the free area of the cutting elements.

Also, the trabecular structures 10 may be different at different locations across the tool. For example, lattice structure and size may be influenced by the cutting edge design used at that location, and strut 12 geometry may vary even within one lattice structure.

Inner trabecular structures of tools such as reamers and drills may be arranged spiraling with a direction against the rotational direction of the tool 1, starting at the cutting elements 4, and with decreasing volume towards the center axis, defining empty recesses or cavities 22 increasing from the cutting edges 6 to the center, in order to prevent jamming of the ablated tissue material within the tool. FIG. 5 shows such a spiraling structure.

In a rasp, the internal trabecular structure portions may similarly decrease in volume, starting at the cutting elements and in a direction against cutting direction towards the center.

Structural features of the surgical tool may be adapted to each specific usage scenario based on simulations and numerical analysis, such as a finite element method (FEM) analysis. Input values for such calculations may comprise required size and shape of the instrument 1, material, usage variants, required cutting forces, cutting resistances of tissue, and/or others. Dynamical considerations for tool stability might be included, as well as long-term wear, especially for non-disposable tools.

Such input variables might either be chosen by a user from a predefined selection of values and conditions, or might be selected without constraints by the user. For example, a software module could be provided where several surgical conditions and applications, or specific implants from a manufacturer, are displayed for selection, such that the user does not need to know extensive details of the required materials and shapes of each tool. Those details could be predefined in a database or software portion. A user might then choose e.g. a reamer for hip implant surgery of certain type and be prompted to input required dimensions or other details, such as patient details. Alternatively or in addition, selection of variables could be performed in a sequential user dialog, where required fields of data are polled based on previous answers. In other embodiments of the invention, input values for numerical simulation of optimized tools may be obtained from other modules or external data sources.

In this way, customized tools for very specific settings can be selected, designed and modelled.

In response, the analysis may then return the structural details of the tool in the form of output values, including required thickness of structures, shape, size, and type of lattice elements, partial and overall dimensions of the tool, indication of solid and hollow portions, and so on. Software modules may either provide resulting output values to a user, store values in a database, forward values for further processing to another module, or may form from those values a complete digital model which can then be further processed for manufacturing, as an input file for manufacturing methods. Standard formats known in the art may be used for modelling the tool and as file format.

Due to the internal structure of the inventive tools, three-dimensional additive manufacturing processes are particularly suited for producing tools and instruments according to the invention. Such methods are based on successive layers of material which are formed from a data model to create an object. The materials for such manufacturing processes in general may include polymers, rubbers, metals and metal alloys, ceramic materials, matrix materials, hybrid materials such as cermet, and others. For tools and instruments of the present invention, materials may be chosen based on structural and functional requirements and might also be combined with each other.

As an example, metals and metal alloys may be used in additive manufacturing processes based on laser sintering, laser melting, electron beam melting, lamination, 3d printing, and extrusion deposition. Raw material for such methods may be present e.g. in the form of powder, granulate, wires, filaments, laminates, and others. Many of these methods are available for metals and alloys of any kind, ceramic materials, polymers, hybrid materials and others. The skilled person is familiar with a large number of such additive manufacturing methods and their details, and not every detail of those methods will be described here. One will also recognize that other manufacturing methods can be applied with and adapted to embodiments of the present invention, as long as those methods are able to produce the required internal structures for a tool.

Optionally, tools and tool parts manufactured by such methods can further be processed, e.g. by adding coatings to the surface or by curing surfaces in order to obtain better cutting characteristics and tool strength.

Depending on the specific manufacturing method and on the requirements of the resulting product, such methods may be used similar to rapid prototyping for single tools and unique demands, and/or may be employed in mass manufacturing, e.g. for providing disposable tools compatible to specific implants. Also, the step of simulating the required tool structure may be directly integrated into the manufacturing process or may be performed completely separately.

Figure 7:
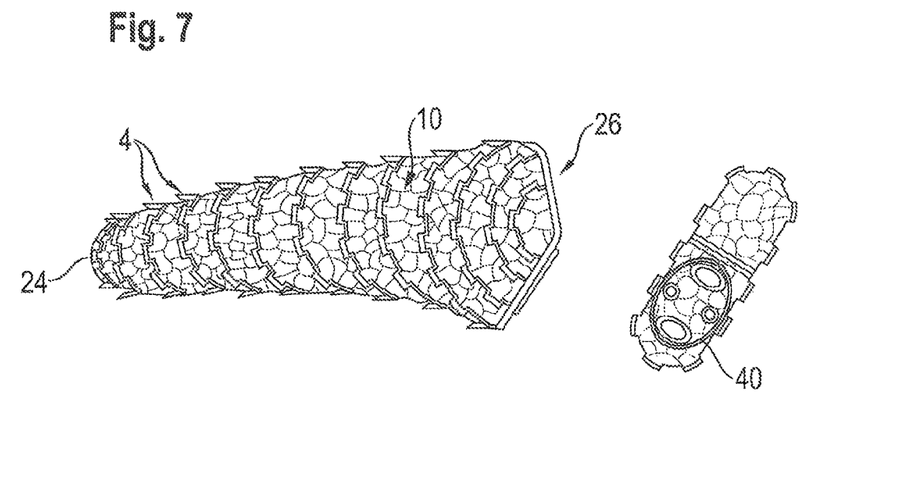
FIG. 7 shows a lateral and a bottom view of a tapered rasp according to another embodiment of the invention.

FIG. 7 depicts another exemplary embodiment of the invention in the form of a rasp 1. The tool body 1 has a round elongate shape. Here, cutting edge elements 4 are disposed in a wedge-shaped arrangement across the surface 2, the wedge axis being shifted from the central axis in order to obtain a directional force. The wedged lines point towards the front end of the tool. As seen in the bottom view, the tool body 1 may again comprise connecting/mounting portions 40 for driving and holding elements.

FIGS. 8 to 15 provide some further examples for the tool body geometry of embodiments of the present invention.

Figure 8:
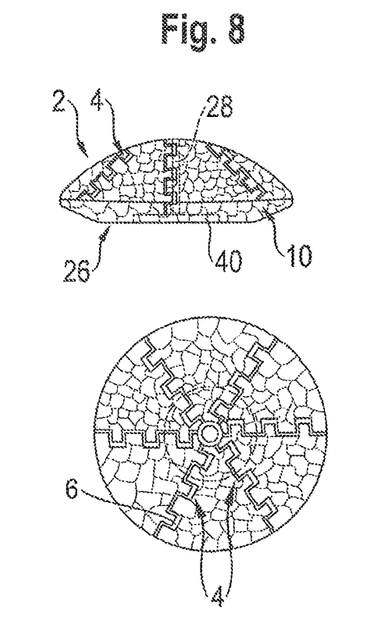
FIG. 8 shows lateral and top views of a thither embodiment of a spherical segment reamer according to the invention.

In FIG. 8, a reamer similar to that of FIG. 1 is shown, where a spherical segment body 1 is provided with cutting edges 6 along radial lines meeting at the apex 24. The bottom surface 26 may be smaller than the largest cross section by adding an inward tapered body portion below the spherical segment, but it also can be intruded into the spherical element.

Figure 9:
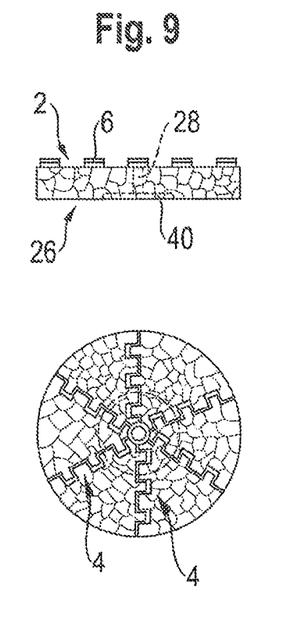
FIG. 9 shows another embodiment of a cylindrical reamer according to the invention.

FIG. 9 then shows a flat cylindrical alternative, again with radially extending cutting elements 4 which are here arranged on the flat cylindrical end face 2. Again, the bottom portion may be tapered inwards or provided with the same circumference.

Figure 10:
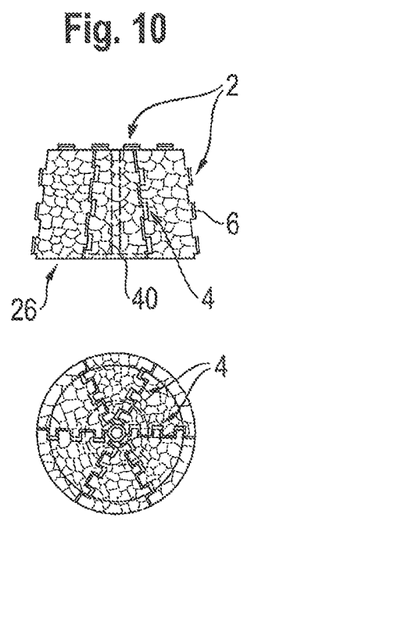
FIG. 10 shows lateral and top views of a further embodiment of a reamer in the shape of a truncated cone according to the invention.

In FIG. 10 a chamfered cylindrical reamer is shown, i.e. having a tool body 1 shaped as a truncated cone. In the present example, cutting elements 4 are arranged both on the truncated upper surface 2 and the lateral surface 2, as can be seen from the cross section. The cutting elements 4 may run in continuous lines across the truncated edge, as shown in the figure, or might be arranged differently on the two surfaces 2.

Figure 11:
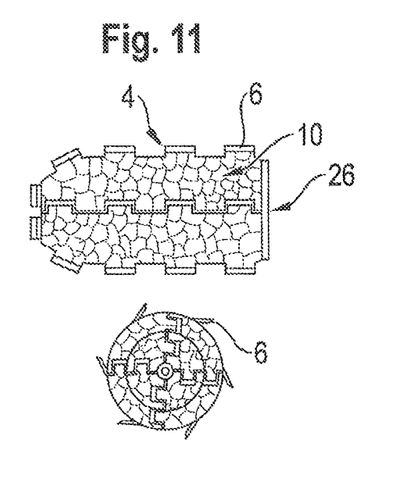
FIG. 11 shows lateral and top views of a cylindrical drill embodiment.

FIG. 11 shows another cylindrical, rather elongate reamer or drill. The top view below shows how cutting elements 4 are arranged both on the upper surface 2 having a reduced radius compared to the tool body 1, and along the lateral surface 2.

Figure 12:
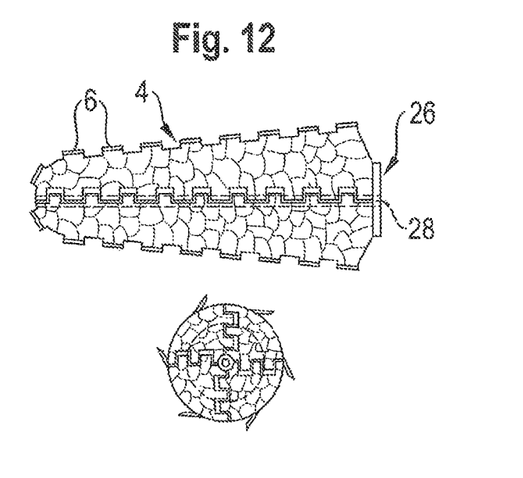
FIG. 12 shows lateral and top views of another tapered drill embodiment.

FIG. 12 is another exemplary drill, which is similar to that of FIG. 11 in its elongated shape and the reduced radius of the end surface, but in addition is tapered towards its end, i.e. the body radius is continuously decreased towards the top.

Figure 13:
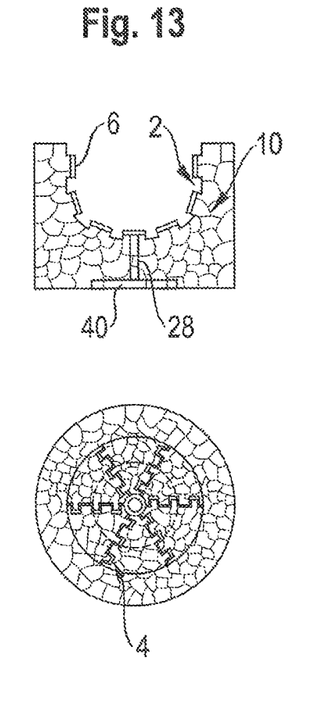
FIG. 13 shows lateral and top views of another exemplary reamer embodiment with an interior reverse dome like active reaming cavity.

FIG. 13 shows another special example of a reamer which might be used for preparing a femoral head or similar bone structures, such as finger bones, in e.g. resurfacing surgery. In this case, the tool body 1 has a hemispherical recess which is adapted for receiving the bone structure, and the cutting elements 4 are provided within the recessed cavity. Otherwise, the general structure is similar to the tools described before; cutting elements 4 in this example are, although inversed in structure, also provided in linear arrangements on the recessed cutting surface 2.

Figure 14:
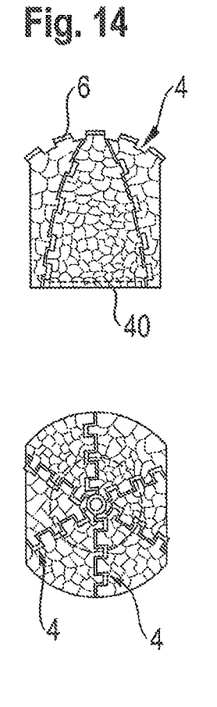
FIGS. 14 and 15 are still further exemplary reamer variants of the invention for minimal invasive surgeries.
Figure 15:
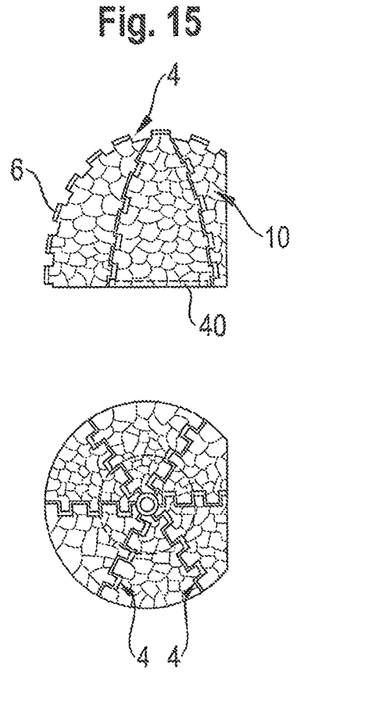

FIGS. 14 and 15 depict further embodiments of reamers, but with partial tool body geometry. As can be seen, both reamers are based on a hemispherical reamer such as that of FIG. 1-4, but segments of the hemisphere are truncated on one (FIG. 15) or more (FIG. 14) sides. The truncation leaves one or more flat, vertical, lateral surfaces, which may be parallel as in FIG. 14, but might also be arranged differently. Such tools are particularly useful for surgery with small incisions such as minimal invasive surgery or other situations with reduced operating area, since the tool body geometry facilitates introducing and retracting the tool, but still results in the same bone cavity due to tool rotation. Of course, this principle of reduced tool body size may be applied to other tools and shapes as well.

Also shown in FIGS. 8 to 13 is a shaft channel 28 which may be included in any tool body for introducing an alignment shaft or alignment pin into the tool, which facilitates correct alignment during machining. A corresponding opening may be present in the adapter plate 40 at the tool bottom 26.

Figure 16:
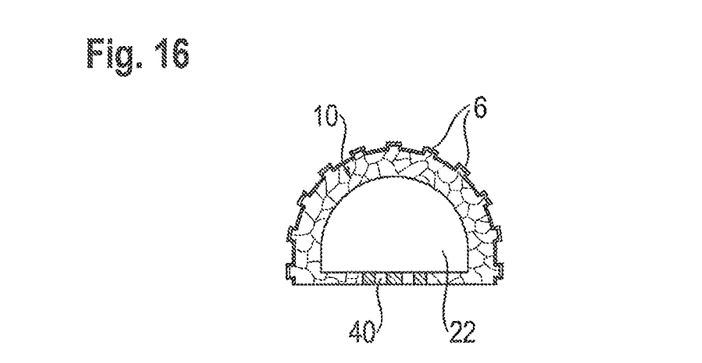
FIG. 16 shows a vertical cross section of an exemplary reamer with a peripheral trabecular and internal hollow structure.

FIG. 16 shows another cross section of an exemplary tool. In this case, the internal structure of the tool (such as a reamer) is provided by a trabecular structure 10 forming a hull portion of defined thickness, which is followed by an internal hollow void 22. The dome layout also provides stability to the tool, while the trabecular wall structure reduces material requirements.

As another exemplary embodiment, a collapsible reamer 1 is presented, as shown in FIGS. 17 to 22.

Figure 171:
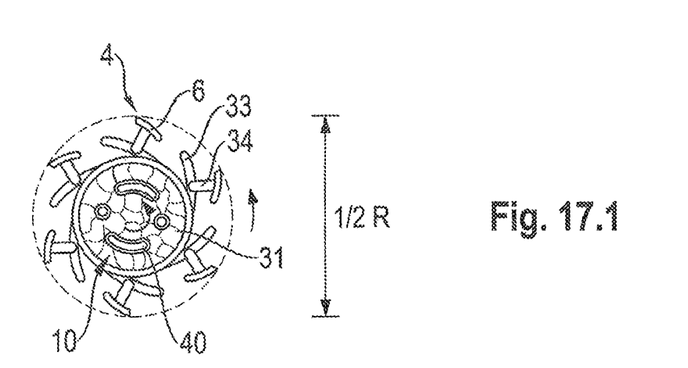
Figure 172:
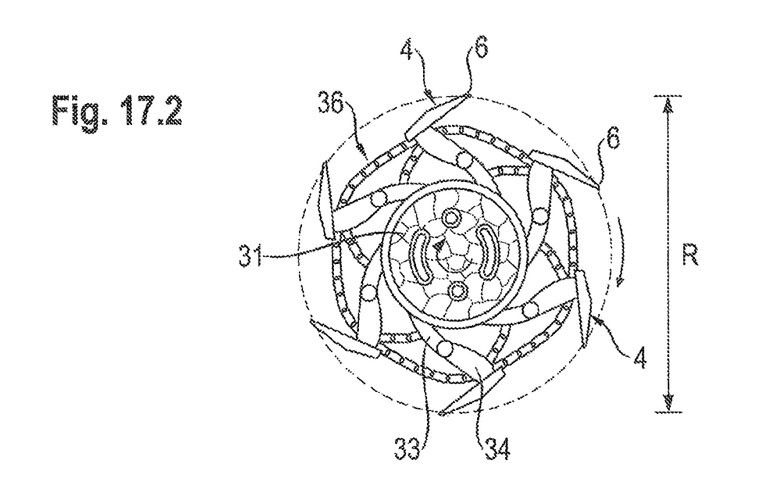

The general structure comprises a central core 31 such as a cone, a cylinder or truncated cone. This core body 31 may be provided with a full or partial trabecular lattice internal structure 10 just as previously detailed for other tools. At the upper end or apex 24 of the core, fixed cutting edge elements 4 may be arranged. Then, rings 33 are provided around the circumference of the core, fixed or connected to the lateral surface. These core rings 33 are not necessarily circular, but may be elliptical or any other shape. Movable, rigid cutting elements 4 including a number of cutting edges 6 are fixedly attached to one or more guiding rings 34, which are interlocked with the core rings 33, as seen in FIG. 17. This combination of interlocked ring elements 33, 34 guides and limits the movement of and stabilizes the rigid cutting elements 4. That is, in this collapsible reamer embodiment, cutting elements 4 comprise a number of cutting edges 6 and a supporting portion on which the cutting edges 6 are formed, such as an elongate flat member.

Figure 18:
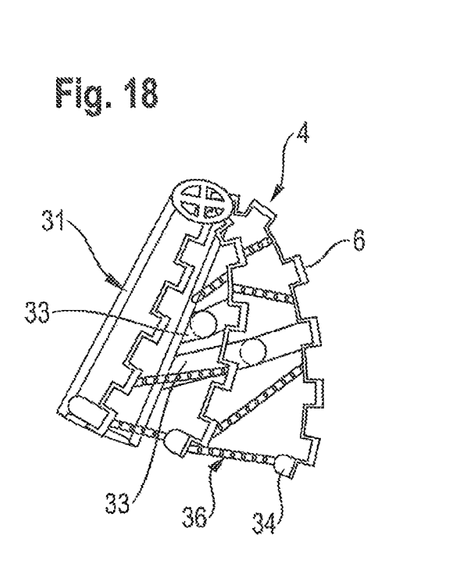
FIG. 18 is a partial cross section of an expandable reamer.
Figure 19:
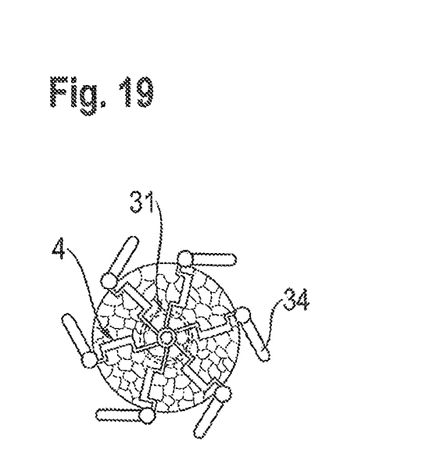
FIG. 19 is a cross section of an expandable reamer body core showing the attached guiding rings.

Further, each cutting element 4 may be attached to a number of chain elements 36 at different locations, see FIG. 18, with the distant end of the chain 36 being attached to the core or another cutting element 4, preferably an adjacent cutting element. Such chains 36 may also be formed from only two linking rings, but preferably include more chain links, and chains may also be interconnected by additional rings or may split into two outer or inner chains by nesting more than two rings, as desired. Instead of ring links, other suitable chain variants may be used. FIG. 19 is a top view showing the core 31 with guiding rings 34 tangentially on its external surface.

The cutting elements 4 are thus formed as solid elements including cutting edges, or may also have an internal lattice structure just as the outer portion of the previous embodiments. FIG. 19 shows another embodiment presenting the cutting elements 4 on the upper surface 2 as well as the hooking ring elements connected to the core 31, without showing the cutting elements or further rings.

The chain structures 36 combined with the movable cutting elements 4 provide a collapsible or foldable tool structure. FIG. 17 illustrates the collapsing function in cross section. Since the chain links/rings 33, 34, 36 are not fixedly connected to each other, but merely nested together or interlinked, length of each chain may vary considerably. In a closed or collapsed position (FIG. 17.1), all rings are pushed together closely, thus providing a tool 1 with minimal radius. When all chains and connected rings are extended to their maximum length (FIG. 17.2), the tool is in an open stable position with maximum tool diameter. The additional chains 36 limit direction and location of the cutting edge elements 4.

Figure 20:
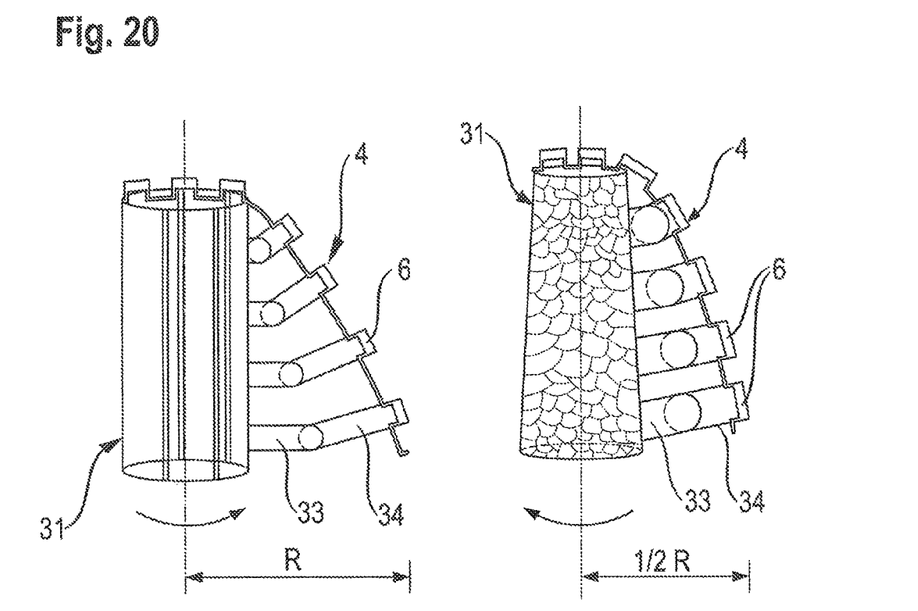
FIG. 20 shows the connecting rings of an expandable reamer in open and closed positions.

The view of FIG. 20 further explains the functionality of the collapsible tool embodiment. For reasons of simplicity, only a single cutting element 4 is shown here. Each cutting element 4 is, with an upper end, movably attached directly to the upper edge of the core 31, e.g. via a core ring fixedly attached within this area. The core rings 33 fixed to the core 31 increase in size towards the bottom and thus define the unfolding geometry of the tool. Corresponding guiding rings 34 are attached to the cutting elements 4, also increasing in size towards the bottom. In this way, the unfolded tool also obtains an essentially hemispherical shape, based on the shape of the cutting elements 4 and the combined length of interlocking core ring 33 and cutting elements guiding ring 34.

The embodiment as shown provides automatic unfolding and folding of the rotated tool based on rotational direction. When the tool 1 is rotated in one direction (clockwise in this example), the cutting elements 4 are guided towards the maximum exterior, i.e., unfolded, position and is thus ready for cutting procedures. Rotating the tool 1 in the opposite direction, i.e. counter-clockwise, pushes the guiding rings 34 towards the tool core 31 and thus folds the tool into its minimum diameter or closed position, while also directing the cutting edges 6 at least partially towards the core 31 and thus essentially removes cutting features of the tool in that position. Such a tool is advantageous in minimal invasive surgery with small incisions, where introducing and retracting a tool might otherwise injure surrounding tissue.

It will be understood that, once again, a hemispherical tool is merely one possible embodiment, and other shapes may be implemented in a similar way using interlocked ring elements 33, 34 fixed to a core 31 and a blade element 4, respectively. Also, rasps may be provided with a collapsible structure, just as reamers. Also, any of the blade structures, internal geometries, blade geometries and other characteristics described for fixed tools above may be transferred to collapsible embodiments, where feasible.

Just as for the rigid surgical tools, collapsible tools according to embodiments of the invention can be manufactured using 3d additive manufacturing processes as described above in detail. The characteristics of such processes allow for obtaining separate, but interlinked parts such as chain links without any further manufacturing steps and therefore considerably improve speed and cost of the manufacturing process.

FIG. 21 depicts some examples of elements to be attached to a surgical tool according to the invention. These might be different types of handles and drills for driving the attached tool head as known in the art, and may be attached via the adapter plate/connecting portion 40 at the bottom 26 of the instruments, but also other link geometries are possible.

FIG. 22 is an example for a press device 50 for disposing of used surgical tools and collecting of tissue material for bone grafting. A tool body 1 is inserted into a receptacle 52 of the press 50 which includes a perforated bottom surface, and a stamp element 54 is moved downwards for crushing the surgical tool head. The compressing force automatically removes tissue material collected within the tool body during use, which can then drop through the perforated bottom into a receptacle for disposal or grafting needs, while at the same time the tool 1 itself is compressed into a flat element. This compressed tool can then easily be wrapped, sterilized and securely forwarded for recycling and disposal.

It will easily be understood that all of these different tool body geometries and cutting element designs could also be combined with each of the teachings above. Instead of reamer cutting elements 4, such tool bodies could be provided with rasping cutting elements, for example by arranging cutting elements 4 in essentially horizontal and parallel lines (perpendicular to the direction shown in FIG. 8-15 for the cutting edge lines). Radial line arrangement of cutting elements as shown may be replaced or complemented by radial cutting elements spiraling around the tool body, single cutting edges 6 placed regularly or irregularly across the surface 2, or others. Radial lines of cutting elements 4 do not necessarily need to start at the apex 24 of the tool surface 2. Also, the number of cutting elements 4 and edges 6 may vary.

For all these body designs, the inner trabecular structure 10 may be adapted as required to obtain necessary cutting forces and tool stability.

It will be understood that the tools and methods according to the invention can also be used for multiple-use tools and are not necessarily limited to disposable tools. Nevertheless, the ease of modelling and producing custom-made tools with low material cost in accordance with inventive embodiments facilitates single-use applications.

Also, while additive manufacturing techniques are getting more widespread and sophisticated, it is also possible to combine such techniques with other manufacturing processes, such as providing a cast metal part as a basis for adding a trabecular structure by 3d-methods, or in any other desirable way. Three-dimensional additive processes, however, provide an easy way to obtain closed or essentially closed trabecula structures or other more complicated internal geometries which cannot be produced by casting methods.

The invention claimed is:

1. A surgical trabecular tool for manipulating or removing bone tissue, comprising:
    a tool body;
    a plurality of separate cutting elements provided on a cutting surface of said tool body, each cutting element comprising a plurality of cutting edges;
    wherein said tool body is formed at least in part by a trabecular internal structure that directly supports said separate cutting elements, comprises at least 2 vol % of a total volume of the tool body and is formed by a lattice of material struts forming a regular or irregular lattice structure; and
    wherein said trabecular internal structure is provided along an inner face of said cutting surface, such that a dome structure with a trabecular structured wall is formed.

2. The surgical tool of claim 1, wherein said lattice structure is based on a pyramidal, cubical, honeycomb lattice base.

3. The surgical tool of claim 1, wherein said lattice material struts are formed with a circular, rectangular, triangular, quadrangular, or hexagonal cross-section.

4. A surgical trabecular tool for manipulating or removing bone tissue, comprising:
    a tool body;
    a plurality of separate cutting elements provided on a cutting surface of said tool body, each cutting element comprising a plurality of cutting edges;
    wherein said tool body is formed at least in part by a trabecular internal structure formed by a lattice of material struts forming a regular or irregular lattice structure, the struts directly supporting said cutting elements; and
    wherein said trabecular internal structure comprises at least 2 vol % of a total volume of the tool body and includes multiple supporting columns interconnected and formed from lattice structures and extending from an inner face of said cutting surface towards the center of said tool body.

5. The surgical tool of claim 1, wherein each of said cutting elements includes a plurality of cutting edges arranged radially across said cutting surface.

6. The surgical tool of claim 1, wherein said surgical tool is a bone reamer, rasp, fraise, or drill.

7. The surgical tool of claim 1, wherein said tool body is formed in a hemispherical, spherical, tapered, or cylindrical shape.

8. The surgical tool of claim 1, wherein the trabecular structure comprises an open-cell foam.

9. The surgical tool of claim 4, wherein the trabecular structure comprises an open-cell foam.

10. The surgical tool of claim 1, wherein the trabecular structure comprises a closed-cell foam.

11. The surgical tool of claim 4, wherein the trabecular structure comprises a closed-cell foam.

* * * * *